US009572553B2

(12) United States Patent
Post

(10) Patent No.: US 9,572,553 B2
(45) Date of Patent: Feb. 21, 2017

(54) CANNULATED MEDICAL INSTRUMENT HANDLE WITH A REMOVABLE INSERT

(71) Applicant: Joe Post, Burlington, WI (US)

(72) Inventor: Joe Post, Burlington, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 728 days.

(21) Appl. No.: 14/016,838

(22) Filed: Sep. 3, 2013

(65) Prior Publication Data

US 2014/0371729 A1 Dec. 18, 2014

Related U.S. Application Data

(60) Provisional application No. 61/834,348, filed on Jun. 12, 2013.

(51) Int. Cl.
*A61B 17/00* (2006.01)

(52) U.S. Cl.
CPC ...... *A61B 17/00* (2013.01); *A61B 2017/00464* (2013.01); *A61B 2017/00477* (2013.01); *A61B 2090/0813* (2016.02)

(58) Field of Classification Search
CPC ...... A61B 19/2203; A61B 19/22; A61B 17/00
USPC .......................................................... 606/1
See application file for complete search history.

(56) References Cited

U.S. PATENT DOCUMENTS

| 5,957,888 A | 9/1999 | Hinchliffe |
| 7,081,122 B1 * | 7/2006 | Reiley ............... A61B 17/34 604/164.01 |
| 8,369,935 B2 | 2/2013 | Ryan |
| 8,377,089 B2 | 2/2013 | Lipchitz et al. |
| 2005/0090841 A1 | 4/2005 | Morrison |
| 2006/0074434 A1 | 4/2006 | Wenstrom et al. |
| 2011/0301613 A1 * | 12/2011 | Green, II ............. A61B 17/92 606/99 |

FOREIGN PATENT DOCUMENTS

EP 0716832 A1 6/1996

* cited by examiner

*Primary Examiner* — William Thomson
*Assistant Examiner* — Dacheng Xie
(74) *Attorney, Agent, or Firm* — Absolute Technology Law Group, LLC

(57) ABSTRACT

A cannulated medical instrument handle apparatus comprised of a handle housing component with a hollow handle insert channel and a removable tubular insert that fits within the handle insert channel. Tubular insert has a hexagonal segment adapted to fit within a recessed hexagonal aperture within the handle insert channel, thereby connecting the handle housing component and tubular insert. Tubular insert also has a tubular shaft segment and a lumen running through its center.

18 Claims, 4 Drawing Sheets

CANNULATED MEDICAL INSTRUMENT HANDLE WITH A REMOVABLE INSERT

CROSS-REFERENCE TO RELATED APPLICATIONS

This application claims priority to U.S. Provisional Application No. 61/834,348 filed on Jun. 12, 2013.

FIELD OF INVENTION

This invention relates to the field of medical devices, and more specifically to a cannulated medical instrument handle structurally adapted for high temperature sterilization of inner core elements.

TERMS OF ART

Figure 1:
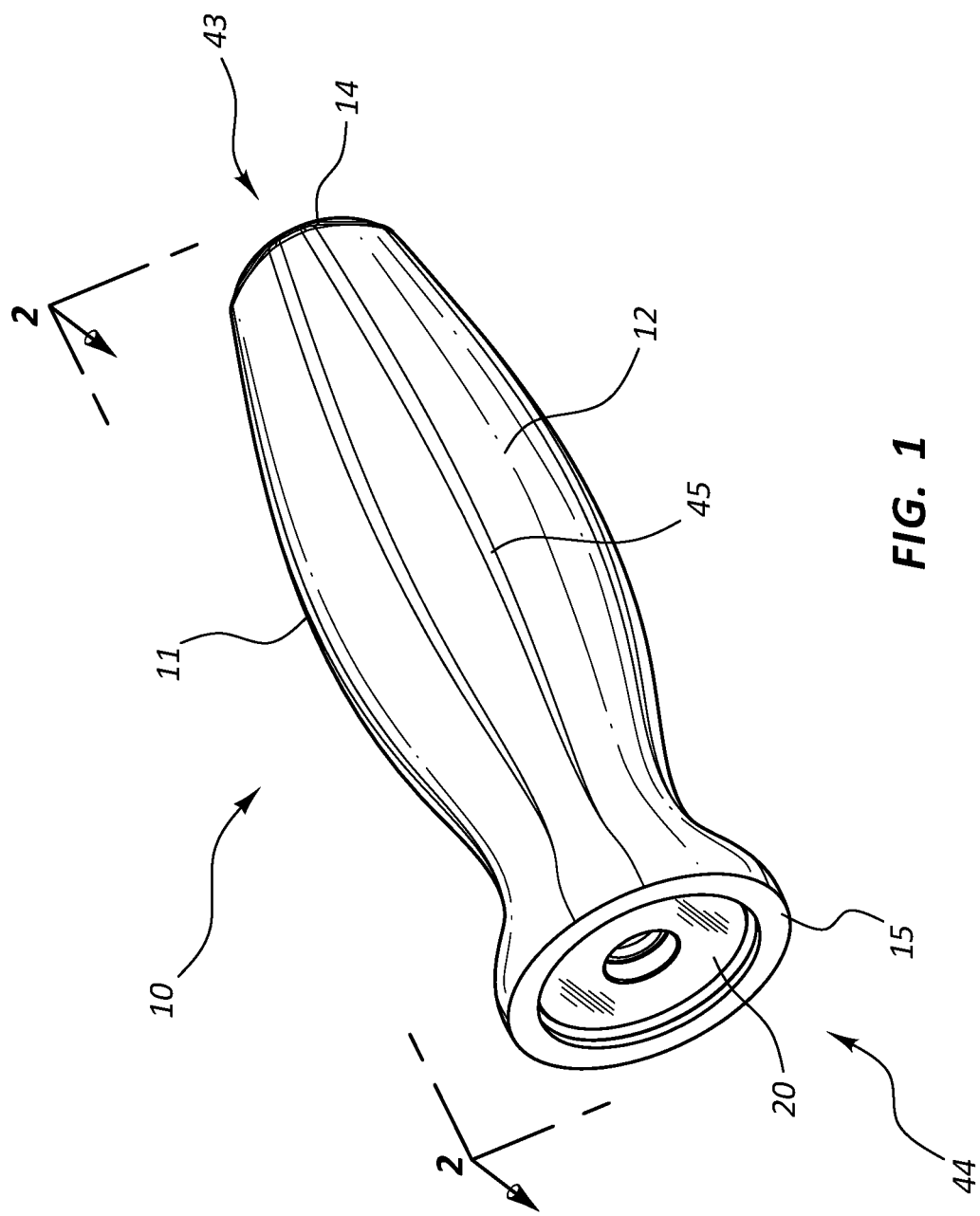
FIG. 1 illustrates an isometric view of a cannulated medical instrument handle in assembled state.

As used herein, the term "channel" means a cannula or hollow shaft that runs through the center of the handle housing component, from the distal insert aperture to the proximal insert aperture.

As used herein, the term "conformed" means structurally configured to conform to geometric dimensions and characteristics.

As used herein, the term "convex end" means a rounded end component.

As used herein, the term "distal" means the location situated further from the user.

As used herein, the term "exterior diameter $D_{handext}$" means the measurement taken from the top exterior surface of the handle housing component to the bottom exterior surface of the handle housing component, taken at any point along the handle housing component.

As used herein, the term "exterior diameter $D_{tubext}$" means the measurement taken from the top exterior surface of the tubular insert to the bottom exterior surface of the tubular insert, taken at any point in the tubular shaft segment of the tubular insert.

As used herein, the term "integrally formed" means machined as a single component or fixedly attached to form a unitary component.

As used herein, the term "interior diameter $D_{thrint}$" means the measurement taken from the top interior surface of the lumen to the bottom interior surface of the lumen, taken at any point within the lumen that comprises a threaded section.

As used herein, the term "interior diameter $D_{smint}$" means the measurement taken from the top interior surface of the lumen to the bottom interior surface of the lumen, taken at any point within the lumen that comprises a smooth lumen.

As used herein, the term "interior diameter $D_{chanint}$" means the measurement taken from the top interior surface of the handle insert channel to the bottom interior surface of the handle insert channel, taken at any point within the second interior section of the insert channel.

As used herein, the term "interior diameter $D_{recint}$" means the measurement taken from the top interior surface of the handle insert channel to the bottom interior surface of the handle insert channel, taken at any point within the proximal receiver section of the insert channel.

As used herein, the term "length L" means the length of the spring, measured from the top of the spring to the bottom of the spring.

As used herein, the term "lumen" means a cannula or hollow shaft that runs through the center of the tubular insert, from the proximal end to the distal end.

As used herein, the term "proximal" means the location situated nearer to the user.

As used herein, the term "recessed" means set within a contour, aperture, channel or hole.

As used herein, the term "secure" means adapted to resist movement.

As used herein, the term "second interior section" means the hollow middle section of the handle insert channel with interior diameter $D_{chanint}$.

As used herein, the term "spring constant S" means the stiffness of the spring, measured by the amount of force that would be required to compress the spring.

BACKGROUND

Among hospital patients that have surgery, it is estimated that approximately 2 percent develop a surgical site infection (SSI), and among those who develop an SSI, it is estimated that approximately 3 percent die as a result. It is a problem known in the art that unclean medical instruments are one direct cause of SSIs. Despite scrupulous adherence to cleaning and sterilization standards, which include a multi-step process of rinsing, scrubbing and sterilization, instruments may fail to become sufficiently clean or sterile.

Cleaning and sterilization of cannulated instruments is particularly challenging. A cannulated medical instrument contains a hollow shaft, known as a lumen, running straight through the center of the instrument, through which a surgeon may introduce, position, manipulate and/or remove surgical and biological material directly to or from the surgical site inside the patient's body. Operating through the center of a medical instrument allows a surgeon to operate with great precision and through a smaller incision, creating the potential for reduced trauma and a better surgical outcome. However, it is a problem known in the art that the interior of a narrow lumen can be difficult to clean and sterilize.

Every surface of a medical instrument must be cleaned and sterilized between uses, including lumen's interior surface. Rinsing and scrubbing steps in the cleaning process should remove physical debris, but then the entire interior surface of the lumen must reach sterilization temperature in an autoclave in order to effectively kill pathogens and meet sterilization requirements. Changing standards in how instruments are sterilized in an autoclave (e.g., reduced cycle time in the autoclave; increased use of autoclave bins with few access holes to allow superheated steam to directly contact instruments) have made sterilization more difficult to achieve than ever before, and some prior art handles may no longer be able to meet sterilization requirements.

Autoclave tests of prior art cannulated medical instruments have demonstrated that instruments with narrow interior diameters in the lumen take longer to reach sterilization temperature in the middle of the lumen as compared to instruments with wider interior diameters in the lumen.

This may be attributed to the greater volume of the structure surrounding a narrower lumen.

It is desirable to have a medical instrument which offers the surgical benefits of a cannulated instrument but which is capable of being sterilized and cleaned in a manner that meets sterilization requirements and thus prevents SSIs.

It is further desirable to have a cannulated medical instrument with a removable, separately sterilized internal lumen to increase the effectiveness of sterilization in an autoclave.

SUMMARY OF THE INVENTION

The present invention is a cannulated medical instrument handle apparatus comprised of a handle housing component that is partially enclosed within a conformed outer silicone layer and a tubular insert that can be removed from the handle housing component using a critical panel and eyelet hole release assembly.

The handle housing component has an inner surface and an outer surface, and it also has a substantially closed convex end, a receiving end, and a hollow handle insert channel. The receiving end of the handle housing component has a round housing aperture which is integrally formed with a recessed hexagonal aperture adapted to receive the tubular insert.

The tubular insert has a distal flat end, a hexagonal segment adapted to fit within the recessed hexagonal aperture, a tubular shaft segment, and a lumen running through its center. The recessed hexagonal aperture contains eyelet shaped grooves located in its interior rectangular panels.

The hexagonal segment contains spring and ball bearing locking assemblies within its exterior rectangular panels, and these spring and ball bearing locking assemblies are designed to engage with the eyelet shaped grooves to secure the tubular insert within the handle housing component.

The tubular insert has a substantially constant exterior diameter $D_{tubext}$, the distal threaded lumen within the tubular insert has an interior diameter $D_{thrint}$, and the proximal smooth lumen within the tubular insert has an interior diameter $D_{smint}$.

The tubular insert exterior diameter $D_{tubext}$ is much smaller than the diameter of the handle housing component as a whole. This ensures that the tubular insert may be removed for sterilization and reinserted once sterile. This also ensures that the insert can also more efficiently reach a target sterilization temperature within an autoclave due to its smaller overall size and mass.

DETAILED DESCRIPTION OF INVENTION

For the purpose of promoting an understanding of the present invention, references are made in the text to exemplary embodiments of a cannulated medical instrument handle, only some of which are described herein. It should be understood that no limitations on the scope of the invention are intended by describing these exemplary embodiments. One of ordinary skill in the art will readily appreciate that alternate but functionally equivalent components and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale. Instead, emphasis has been placed upon illustrating the principles of the invention. Like reference numerals in the various drawings refer to identical or nearly identical structural elements.

Moreover, the terms "substantially" or "approximately" as used herein may be applied to modify any quantitative representation that could permissibly vary without resulting in a change in the basic function to which it is related.

FIG. 1 illustrates an isometric view of a cannulated medical instrument handle 10 with a receiving end 44 and a convex end 43. Handle 10 has an outer silicone layer 11 with raised contour lines 45 and an inner housing 12 which is comprised of heat conducting metal such as aluminum. In the embodiment shown, outer silicone layer 11 surrounds inner housing 12 of handle 10, providing an ergonomic and secure grip to the user with its raised contour lines 45 and silicone construction. A tubular insert 20 is removed from inner housing 12 via housing aperture 15.

Figure 2:
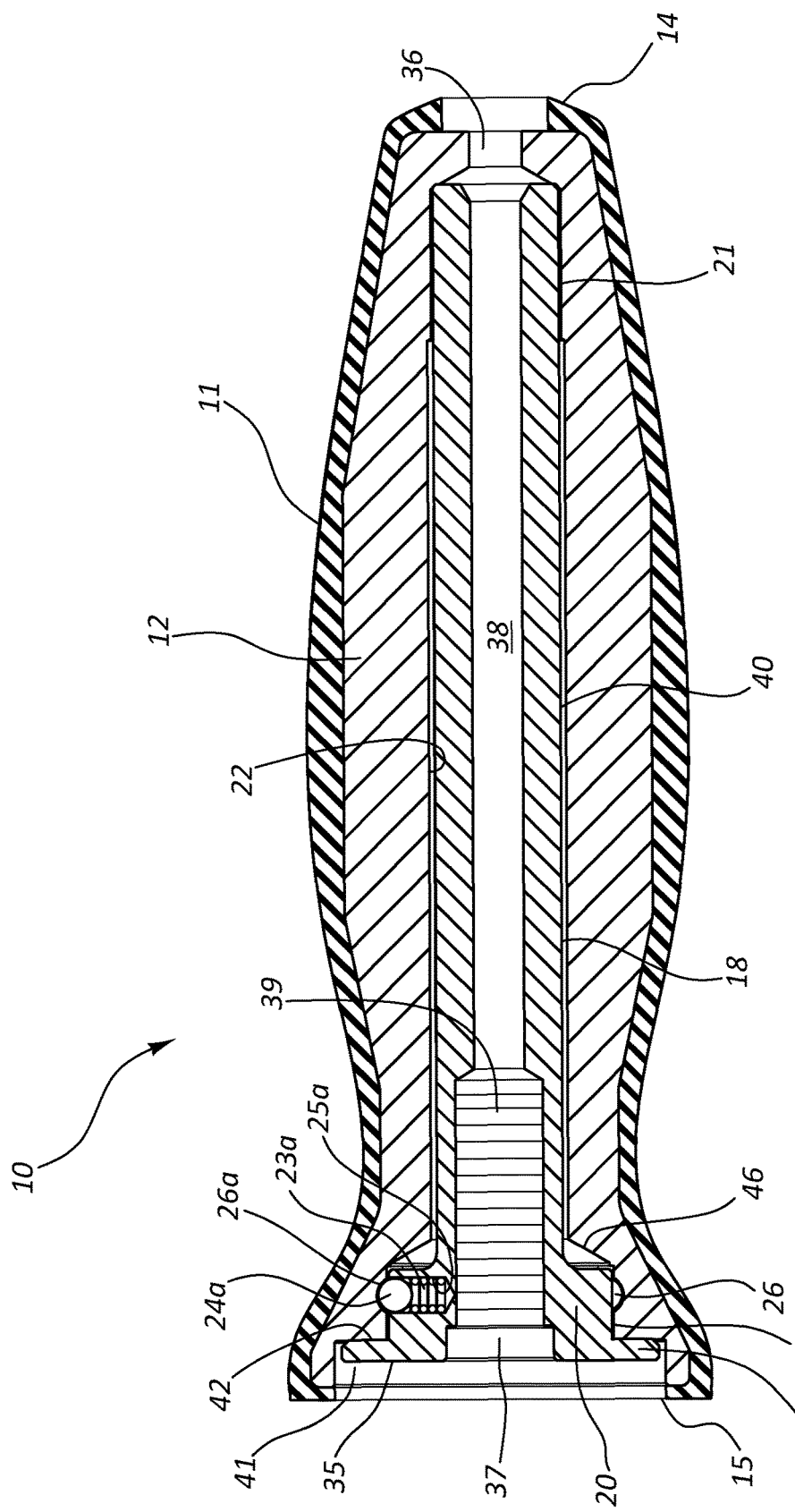
FIG. 2 illustrates a cross-section view of a cannulated medical instrument handle in assembled state.

FIG. 2 illustrates a cross-sectional view of a cannulated medical instrument handle 10 as it appears when assembled. In the embodiment shown, tubular insert 20 is a single machined piece that has a distal flat end 35, a hexagonal segment 28, and a tubular shaft segment 40 containing a lumen 38. Inner housing 12 includes handle insert channel 18, which has several distinct sections or segments: a first distal segment comprised a shallow recess 41 that terminates in a flat exterior surface 42, a recessed hexagonal aperture 16, and a beveled edge 46 that leads to the second interior 22 and proximal receiver 21 sections of handle insert channel 18. The second interior 22 and proximal receiver 21 sections have circular cross-sections. Second interior section 22 has a consistent interior diameter $D_{chanint}$ until it reaches the proximal receiver section 21 with reduced interior diameter $D_{recint}$. At the proximal end of proximal receiver 21, handle insert channel 18 narrows to form proximal insert aperture 36, leading to proximal handle aperture 14.

When assembled, tubular insert 20 fits into handle insert channel 18 through round housing aperture 15. As illustrated in the exemplary embodiment in FIG. 2, round housing aperture 15 is designed to accommodate the distal flat end 35 of tubular insert 20 within shallow recess 41. Hexagonal segment 28 fits into recessed hexagonal aperture 16 and locks into place as ball bearings 24a-24c (24a shown) engage with eyelet shaped grooves 26a, 26c and 26f (26a shown) under pressure from springs 23a-23c (23a shown). Springs 23a-23c have a length L and a spring constant S that are sufficient to positively lock ball bearings 24a-24c into eyelet shaped grooves 26a, 26c, 26f and hold tubular insert 20 inside handle housing component 10. Said length L and spring constant S are not as great as to prevent removal of tubular insert 20.

FIG. 2 also illustrates the interior of tubular insert 20, which contains a lumen 38 that runs substantially the length of tubular insert 20 from distal insert aperture 37 to proximal insert aperture 36. The distal end of lumen 38 contains a section of threads 39 designed to receive medical instruments that can be attached interchangeably to medical instrument handles. When a cannulated instrument is installed, access to the interior of said cannulated instrument is provided through proximal handle aperture 14, proximal insert aperture 36, and lumen 38.

Figure 3:
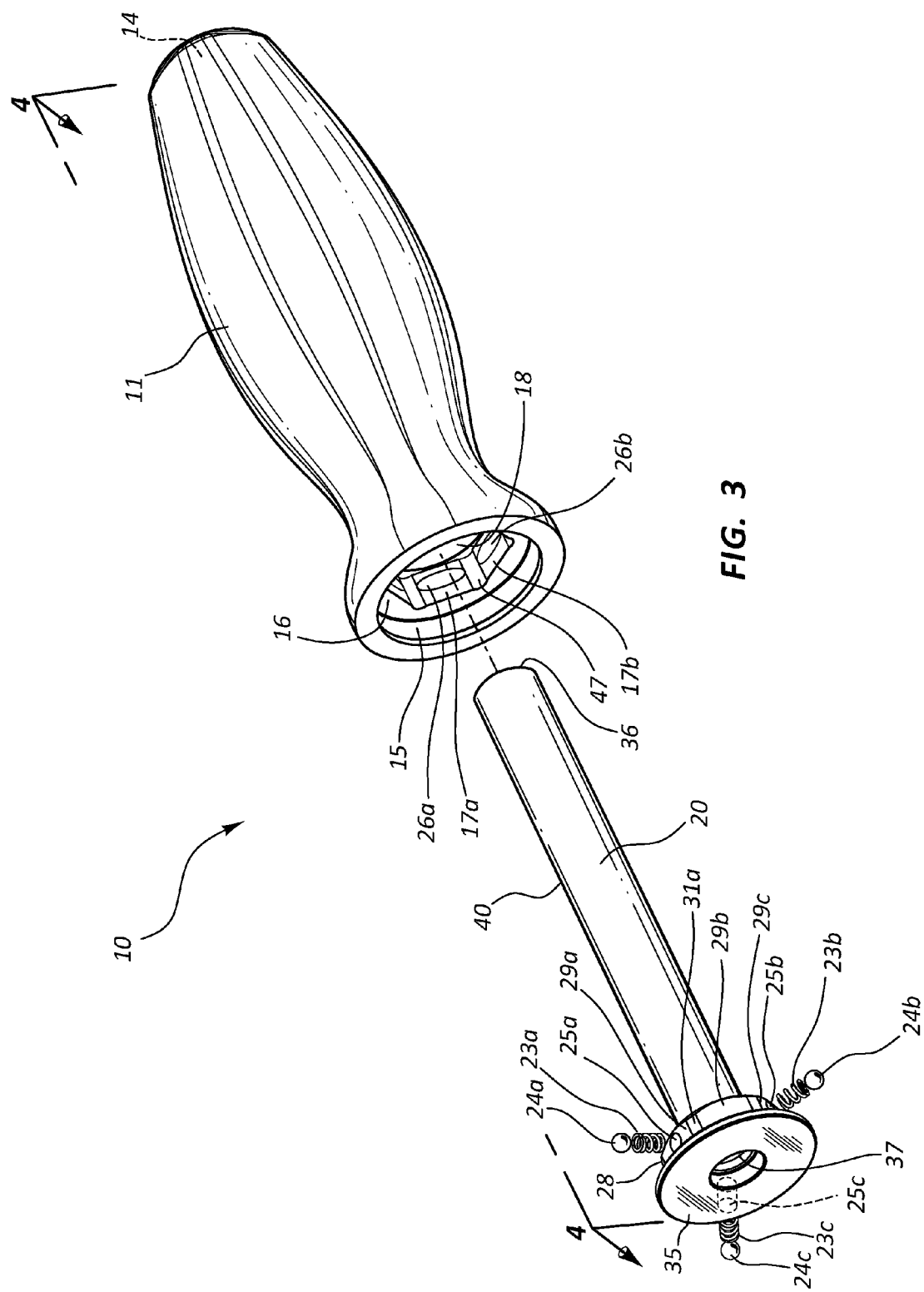
FIG. 3 illustrates an exploded isometric view of a cannulated medical instrument handle.

FIG. 3 illustrates an exploded isometric view of a cannulated medical instrument handle 10, where tubular insert 20 has been removed from handle insert channel 18. Round housing aperture 15 reveals a recessed hexagonal enclosure 16 with interior rectangular panels 17a-17f and eyelet shaped grooves 26a-26f. Handle insert channel 18 runs through the middle of inner housing 12 (not shown) and is open on both ends through round housing aperture 15 and proximal handle aperture 14.

Hexagonal segment 28 is shown with exterior rectangular panels 29a-29c and corner surfaces 31a-31f that fit against interior rectangular panels 17a-17f and corner grooves 47 within recessed hexagonal aperture 16 to prevent axial rotation of tubular insert 20 within handle insert channel 18. In the present embodiment, three spring 23a-23c and ball bearing 24a-24c locking assemblies are located within detent holes 25a-25c in exterior rectangular panels 29a, 29c and 29e (29a shown). Exterior rectangular panels 29b, 29d and 29f (29b shown) do not contain detent holes 25 with spring 23 and ball bearing 24 locking assemblies. Within recessed hexagonal aperture 16, however, all six interior rectangular panels 17a-17f contain eyelet shaped grooves 26a-26f that can engage ball bearings 24a-24c so that tubular insert 20 may lock into handle insert channel 18 in any position where hexagonal segment 28 fits into recessed hexagonal enclosure 16. As further illustrated in FIG. 3, tubular insert 20 has a distal flat end 35 and a hexagonal locking segment 28 with exterior surfaces 29a-29f (29a-29c shown) that contain detent holes 25a-25c and spring 23a-23c and ball bearing 24a-24c locking assemblies. Other than where it widens at its distal end for distal flat end 35 and hexagonal segment 28, tubular insert 20 has a consistent exterior diameter $D_{tubext}$ along the tubular shaft segment 40 that forms the majority of its length.

Figure 4:
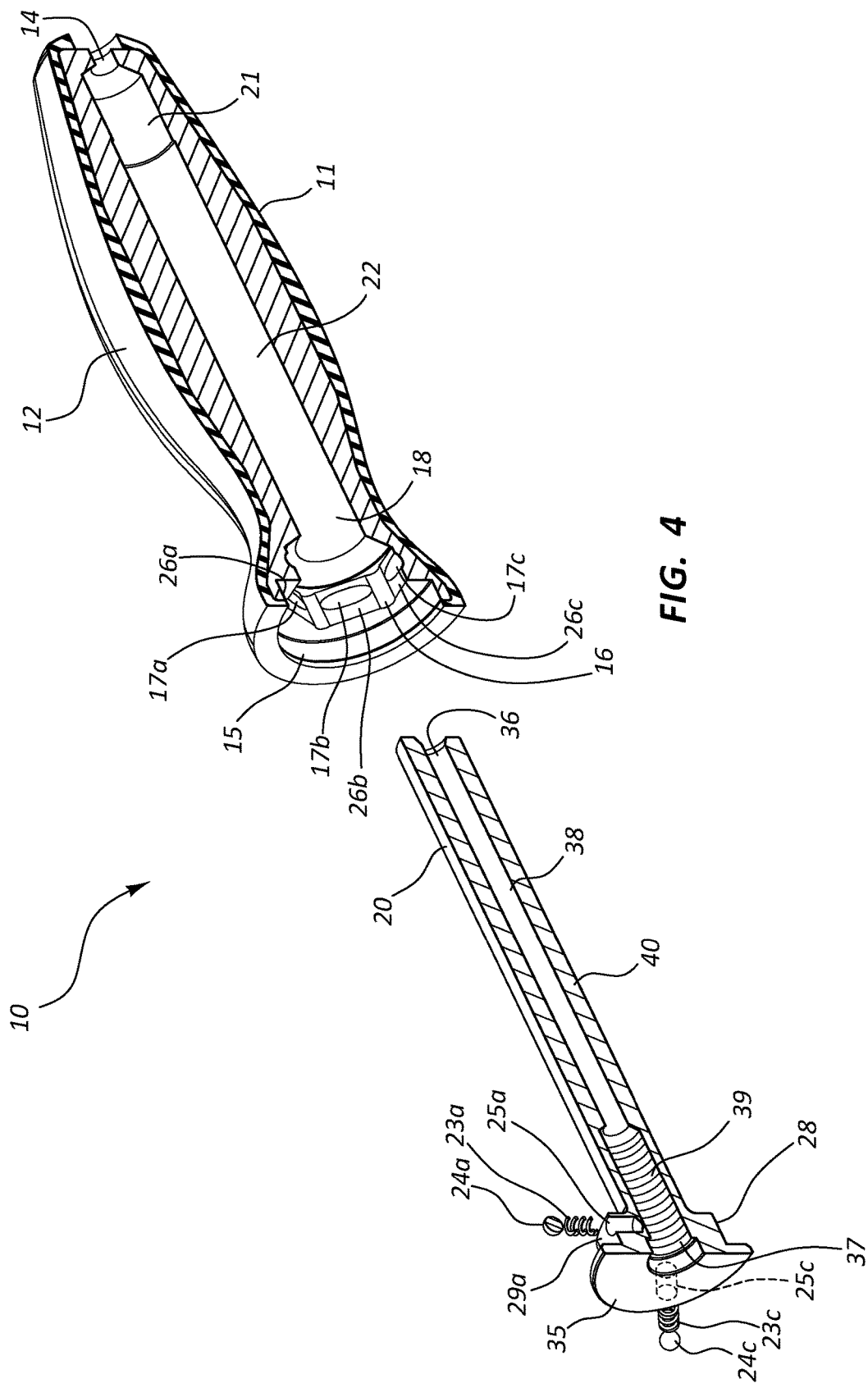
FIG. 4 illustrates an exploded isometric cross-section view of a cannulated medical instrument handle.

FIG. 4 illustrates an exploded isometric cross-section view of a cannulated medical instrument handle 10. The interior of tubular insert 20 contains threads 39 at its distal end near distal insert aperture 37 and a lumen 38 that runs through the center to proximal insert aperture 36. As further illustrated in the exemplary embodiment, tubular insert 20 has a consistent exterior diameter $D_{tubext}$ for substantially the entire length of its tubular shaft segment 40. Handle insert channel 18 has two sections that are adjacent to tubular shaft segment 40 when tubular insert 20 is installed: an interior section 22 with interior diameter $D_{chanint}$ and a proximal receiver section 21 with interior diameter $D_{recint}$. Interior diameter $D_{recint}$ of proximal receiver 21 is sufficiently larger than exterior diameter $D_{tubext}$ of tubular shaft segment 40 so that the proximal end of tubular shaft segment 40 fits securely within proximal receiver 21. Interior diameter $D_{chanint}$ of interior section 22 is larger than interior diameter $D_{recint}$ of proximal receiver 21. This provides a large interior section 22 within handle insert channel 18 that efficiently reaches sterilization temperature in an autoclave when cannulated medical instrument handle 10 is being cleaned.

When disassembled and placed in an autoclave for sterilization, the present embodiment consists of a separate handle 10 and tubular insert 20 that are each adapted to efficiently reach sterilization temperature. Handle 10 contains handle insert channel 18 with interior chamber 22 that has interior diameter $D_{chanint}$. Interior diameter $D_{chanint}$ is considerably larger than the interior diameter $D_{smint}$ of lumen 38, which is the standard diameter for a lumen in medical handles known in the art. Therefore, handle 10 has much larger internal channel as compared to a standard handle and may reach effective sterilization temperatures more quickly.

Tubular insert 20 has a standard narrow lumen 38 with interior diameter $D_{smint}$, but the external diameter $D_{tubext}$ of the tubular shaft segment is considerably smaller than the diameter of the handle 10, which would be similar to a standard single piece cannulated handle. Thus, tubular insert 20 has much less mass surrounding the lumen 38 as compared to an entire handle and may reach effective sterilization temperatures more quickly.

What is claimed is:

1. A surgical instrument handle apparatus for a cannulated medical instrument comprised of:
    a handle housing component, wherein said handle housing component has an exterior housing diameter $D_{handext}$, a recessed hexagonal aperture, and a segmented handle insert channel;
    wherein said segmented handle insert channel has:
        a first interior segment, having a first segment diameter $D_{chanint}$, and
        a second receiving segment with diameter $D_{recint}$ that is less than diameter $D_{chanint}$;
    wherein said apparatus further includes a removable tubular insert adapted for insertion into said segmented handle insert channel;
    wherein said removable tubular insert has:
        a hexagonal segment adapted to fit within said recessed hexagonal aperture, and
        a tubular shaft segment having an external diameter $D_{tubext}$;
    wherein the outer diameter $D_{tubext}$ corresponds to $D_{recint}$ for insertion;
    wherein said hexagonal segment further includes least one spring and ball bearing locking assembly to secure said tubular insert within said handle housing component;
    wherein said at least one spring and ball bearing locking assembly has at least one storing and at least one ball bearing located within at least one detent hole; and
    wherein said at least one detent hole is located within at least one exterior rectangular panel on said hexagonal segment.

2. The apparatus of claim 1 wherein said handle housing component further has a shallow recess.

3. The apparatus of claim 2 wherein said removable tubular insert has a distal flat end adapted to fit within said shallow recess.

4. The apparatus of claim 3 wherein said distal flat end is adapted to receive an axial force to secure said removable tubular insert within said handle housing component, and a proximal end of said removable tubular insert is adapted to receive an axial force through a proximal handle aperture to release said removable tubular insert from within said handle housing component.

5. The apparatus of claim 1 wherein said internal diameter $D_{recint}$ of said receiving segment is adapted to secure the proximal end of said tubular insert.

6. The apparatus of claim 1 wherein the fit of said hexagonal segment within said recessed hexagonal aperture secures said tubular insert against axial rotation.

7. The apparatus of claim 1 wherein said recessed hexagonal aperture has a plurality of interior rectangular panels and a plurality of corner grooves.

8. The apparatus of claim 7 wherein said hexagonal segment further includes a plurality of exterior rectangular panels and a plurality of corner surfaces that are respectively structurally conformed to fit within said plurality of interior rectangular panels and said plurality of corner grooves.

9. The apparatus of claim 1 wherein said hexagonal segment further includes at least three spring and ball bearing locking assemblies.

10. The apparatus of claim 1 wherein said at least one spring has a length L, wherein said length L has a critical value between about 0.100 inches and about 0.502 inches.

11. The apparatus of claim 1 wherein spring constant S has a critical value between about 0.237 lbf/in and about 13.520 lbf/in to ensure that the insert can be quickly removed for sterilization but is not dislodged during a surgical procedure.

12. The apparatus of claim 1 wherein said recessed hexagonal aperture has a plurality of interior rectangular panels.

13. The apparatus of claim 12, wherein each of said interior rectangular panels has an eyelet shaped groove adapted to receive at least one ball bearing.

14. The apparatus of claim 3 wherein a round housing aperture is designed to accommodate said distal flat end of said removable tubular insert within said shallow recess.

15. The apparatus of claim 1 wherein a distal end of a lumen extending through said removable tubular insert is threaded and operatively connects to a shaft of at least one interchangeable medical instrument.

16. The apparatus of claim 1 wherein $D_{tubext}$ has a critical range between about 0.180 inches and about 0.260 inches to maximize both thermal conductivity and mechanical strength.

17. The apparatus of claim 1 wherein $D_{thrint}$ has a critical range between about 0.156 inches and about 0.250 inches to maximize both thermal conductivity and mechanical strength.

18. The apparatus of claim 1 wherein $D_{recint}$ has a critical range between about 0.180 inches and about 0.380 inches to maximize both thermal conductivity and mechanical strength.

\* \* \* \* \*